United States Patent
Jaracz et al.

(10) Patent No.: US 10,357,438 B2
(45) Date of Patent: Jul. 23, 2019

(54) METAL SALT COMPOSITIONS

(71) Applicant: Colgate-Palmolive Company, New York, NY (US)

(72) Inventors: Stanislav Jaracz, Somerset, NJ (US); Harsh M. Trivedi, Hillsborough, NJ (US); Lyndsay Schaeffer-Korbylo, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/529,635

(22) PCT Filed: Dec. 15, 2015

(86) PCT No.: PCT/US2015/065879
§ 371 (c)(1),
(2) Date: May 25, 2017

(87) PCT Pub. No.: WO2016/100381
PCT Pub. Date: Jun. 23, 2016

(65) Prior Publication Data
US 2017/0258693 A1 Sep. 14, 2017

Related U.S. Application Data

(60) Provisional application No. 62/092,509, filed on Dec. 16, 2014.

(51) Int. Cl.
*A61K 8/27* (2006.01)
*A61K 8/362* (2006.01)
*A61K 8/365* (2006.01)
*A61Q 11/00* (2006.01)

(52) U.S. Cl.
CPC ............ *A61K 8/27* (2013.01); *A61K 8/362* (2013.01); *A61K 8/365* (2013.01); *A61Q 11/00* (2013.01); *A61K 2800/92* (2013.01)

(58) Field of Classification Search
CPC .................................. A61K 8/69; A61Q 11/00
USPC ............................................ 424/49, 42, 56
See application file for complete search history.

(56) References Cited

U.S. PATENT DOCUMENTS

| | | | |
|---|---|---|---|
| 4,289,754 A | 9/1981 | Dhabhar et al. | |
| 4,289,755 A * | 9/1981 | Dhabhar .................. | A61K 8/21 424/49 |
| 4,839,157 A | 6/1989 | Mei-King Ng et al. | |
| 5,695,746 A | 12/1997 | Garlick, Jr. et al. | |
| 5,776,435 A | 7/1998 | Gaffar et al. | |
| 6,015,547 A | 1/2000 | Yam | |
| 9,486,396 B2 | 11/2016 | Maloney et al. | |
| 2011/0097284 A1 * | 4/2011 | Bottner .................... | A61K 8/99 424/48 |
| 2012/0045402 A1 * | 2/2012 | Morgan .................... | A61K 8/27 424/52 |
| 2015/0335541 A1 | 11/2015 | Xu et al. | |

FOREIGN PATENT DOCUMENTS

| WO | WO 1991/011987 | 8/1991 |
|---|---|---|
| WO | WO 1994/014406 | 7/1994 |
| WO | WO 2012/087288 | 6/2012 |
| WO | WO 2014/094225 | 6/2014 |

OTHER PUBLICATIONS

Clever et al., 1992, "The Solubility of Some Sparingly Soluble Salts of Zinc and Cadmium in Water and in Aqueous Electrolyte Solutions," J. Phys. Chem. Ref. Data 21(5):941-966.
International Search Report and Written Opinion in International Application No. PCT/US2015/065879, dated Mar. 16, 2016.
Mitra et al., 1960, "The reaction between polyvalent metal cations and alkali metal pyrophosphates," Proc Nat Inst Sci India, 26A(Supple I):151-161.
Morozova et al., 1976, "Zn2P2O7—K4P2O7—H2O System at 25° C.," Russian Journal of Inorganic Chemistry 21(6):878.
National Academy of Sciences, 1965, "Chemicals Used in Food Processing", Publication 1274, pp. 63-258.

* cited by examiner

*Primary Examiner* — Walter E Webb

(57) ABSTRACT

The disclosure provides oral care compositions comprising zinc ions and citrate ions with molar ratios which unexpectedly high zinc bioavailability, together with methods of preparing and using the same.

20 Claims, No Drawings

METAL SALT COMPOSITIONS

CROSS-REFERENCE TO RELATED PATENT APPLICATIONS

This application claims the benefit of priority to U.S. Provisional Patent Application Ser. No. 62/092,509 filed Dec. 16, 2014, the entirety of which is incorporated herein by reference.

BACKGROUND

The amount of a given metal salt which can be incorporated into an oral care product is often limited as a result of unfavorable effects on the sensory experience of the user, for example, astringency, taste and mouth feel. Zinc is a particularly difficult metal ion to incorporate into oral care compositions, as the concentration at which it is effective as an antimicrobial agent is very close to the concentration at which it is unacceptably astringent.

These limits on metal salt concentration have made it difficult to deliver an effective amount of a metal ion to the soft and/or hard tissue of the oral cavity using an oral care composition. Embodiments of the present invention provide compositions which address, inter alia, this problem.

WO 2012/087288A2, incorporated herein by reference, has disclosed oral care compositions comprising combinations of metal salts, and in particular, combinations of insoluble zinc salts and soluble zinc salts. WO 2012/087288A2 includes in its disclosure combinations of zinc oxide and zinc citrate. However, this reference does not teach specific ratios of net zinc to net citrate, specific pH values, or a combination of zinc chloride and zinc citrate.

SUMMARY

The present disclosure provides, in one embodiment, an oral care composition comprising: a source of zinc ions and a source of citrate ions, wherein the ratio of zinc ions to citrate ions is about 2:1 on a molar basis. In particular embodiments, the composition further comprises a monodentate anion, such as chloride. For example, the composition can include equimolar amounts of zinc chloride ($ZnCl_2$) and zinc citrate ($Zn_3(citrate)_2$) which together can form an ionic complex ($[Zn_2(citrate)]^+Cl^-$). In some embodiments, the total zinc content of the composition is 1.0% by weight or less, preferably 0.5% by weight or less.

Some embodiments provide a method of treating or preventing a disease or condition of the oral cavity comprising contacting an oral cavity surface of a patient in need thereof with any one of the compositions described herein.

Additional embodiments are provided in the detailed description below and in the examples.

DETAILED DESCRIPTION

As used throughout, ranges are used as a short hand for describing each and every value that is within the range. Any value within the range can be selected as the terminus of the range.

In addition, all references cited herein are hereby incorporated by reference in their entireties. In the event of a conflict in a definition in the present disclosure and that of a cited reference, the present disclosure controls.

The inventors have unexpectedly discovered that a molar ratio of zinc to citrate ions of about 2:1 provides enhanced bioavailability and uptake of zinc by soft and hard tissues.

Conventional oral care compositions comprising zinc typically require zinc concentrations in the range of 1.0 to 2.0% or more in order to achieve effective antibacterial effects, but the total zinc uptake when there is molar ratio of zinc to citrate ions of 2:1 is greater than the uptake when there is an equimolar amount of soluble zinc from other sources, e.g., zinc citrate or zinc chloride.

Without being bound by theory, it is believed that the use of a 2:1 molar ratio of zinc to citrate results in the formation of a complex in which two zinc atoms are ligated to one citrate molecule and one or more monodentate anions. In a preferred embodiment, the monodentate anion is a halide, e.g., chloride, and the complex has the empirical formula $[Zn_2(citrate)]Cl$. It is believed that the nature of the zinc complex formed in an oral care composition has an important effect on the concentration of zinc available for uptake (bioavailable zinc). For instance, some zinc complexes have a greater capacity for uptake by bacterial membrane permeation mechanisms (e.g., active and passive transport mechanisms) than other complexes. It is believed that both free soluble zinc and certain zinc complexes are available for uptake by both oral cavity tissues and microorganisms, such that the extent of and nature of the zinc complexes that form in an oral care composition are important factors in determining antimicrobial efficacy.

For example, without being bound by theory, providing equimolar amounts of zinc chloride ($ZnCl_2$) and zinc citrate ($Zn_3(citrate)_2$) is believed to permit formation of the ionic complex ($[Zn_2(citrate)]^+Cl^-$). This complex has a 2:1:1 molar ratio of zinc ions to citrate ions to chloride ions. It is believed that complexes with a 2:1 molar ratio of zinc to citrate, such as the above 2:1:1 zinc-citrate-chloride complex, provide greater bioavailability of zinc to cells than is provided by uncomplexed Zn ions, so that the use of a 2:1 molar ratio of zinc to citrate unexpectedly results in an effective increase in zinc uptake.

In another embodiment, the $[Zn_2(citrate)]^+Cl^-$ complex can be effectively formed by combing zinc oxide, citric acid, and hydrochloric acid in a 2:1:1 molar ratio. Without being bound by theory, it is believed that providing zinc oxide, citric acid, and hydrochloric acid in the appropriate ratio results in the in situ formation of equimolar amounts of zinc chloride and zinc citrate, which then interact to form the desired complex. The interaction can be summarized as follows:

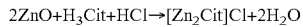

$2ZnO+H_3Cit+HCl \rightarrow [Zn_2Cit]Cl+2H_2O$

In another embodiment, the desired complex can be formed in situ using a 2:1:4 ratio of zinc oxide, sodium citrate and hydrochloric acid:

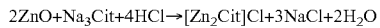

$2ZnO+Na_3Cit+4HCl \rightarrow [Zn_2Cit]Cl+3NaCl+2H_2O$

Thus, the desired $[Zn_2(citrate)]^+Cl^-$ complex can be formed using various combinations of zinc sources, citrate sources and chloride sources in appropriate relative amounts.

The present disclosure thus provides, in one embodiment, an oral care composition (Composition 1) comprising: a source of zinc ions and a source of citrate ions, wherein the ratio of zinc ions to citrate ions is from 1.7:1 to 2.3:1, for example, 1.9:1 to 2.1:1, or about 2:1, on a molar basis. In further embodiments, the present disclosure provides:

1.1. Composition 1, further comprising a monodentate anion (e.g. chloride), wherein the ratio of zinc ions to citrate ions to anion is about 2:1:1 on a molar basis.

1.2. Any foregoing composition wherein the pH of the composition is from 4.6 to 8.6, e.g., from 4.6 to 6.2, e.g. about 5.4.

1.3. Any foregoing composition wherein the zinc source is selected from zinc chloride, zinc citrate, zinc oxide, zinc lactate, zinc nitrate, zinc acetate, zinc gluconate, zinc glycinate, zinc sulfate, zinc oleate, zinc hydroxide, zinc carbonate, zinc peroxide, or a combination of two or more thereof.

1.4. Any foregoing composition wherein the zinc source is selected from zinc chloride, zinc citrate or zinc oxide.

1.5. Any foregoing composition comprising zinc chloride and zinc citrate.

1.6. Any foregoing composition comprising equimolar amounts of zinc chloride ($ZnCl_2$) and zinc citrate ($Zn_3(citrate)_2$), e.g., to form an ionic complex $[Zn_2(citrate)]^+Cl^-$.

1.7. Any foregoing composition comprising $[Zn_2(citrate)]^+Cl^-$.

1.8. Any foregoing composition wherein the citrate source is selected from citric acid or a mono-, di- or tri-basic citrate salt.

1.9. Any foregoing composition comprising zinc oxide and zinc citrate.

1.10. Any foregoing composition wherein the citrate source is citric acid or sodium citrate.

1.11. Any foregoing composition comprising zinc oxide and citric acid.

1.12. Any foregoing composition comprising zinc chloride and sodium citrate.

1.13. Any foregoing composition wherein the total zinc concentration is from 0.01% to 1.0% by weight of the composition; e.g., from 0.1 to 0.5% by weight of the composition for a toothpaste, or, e.g., 0.2 to 0.3% or 0.25% by weight of the composition for a toothpaste; or, e.g., 0.01 to 0.1% by weight of the composition for a mouthwash.

1.14. Any foregoing composition wherein the composition is free of polyphosphates, polyphosphonates, pyrophosphates and/or phosphates.

1.15. Any foregoing composition further comprising one or more components selected from a fluoride ion source; a tartar control agent; a buffering agent; an antibacterial agent; an abrasive; and a combination of two or more thereof.

1.16. Any foregoing composition wherein at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

1.17. Any foregoing composition wherein the composition is a toothpaste, tooth powder, or mouthwash, e.g., a toothpaste.

1.18. Any foregoing composition for use in a method of treatment or prophylaxis of a disease or condition of the oral cavity comprising contacting an oral cavity surface of a patient in need thereof with ant of the preceding compositions; for example, wherein the disease or condition of the oral cavity is halitosis or gingivitis.

1.19. Any foregoing composition, wherein the composition provides greater than 6000 ppm of soluble zinc ion for every 1.0% of zinc by weight of the composition, e.g., after 4 days of agitation.

1.20. Any foregoing composition, wherein the composition provides greater than 3000 ppm of soluble zinc at a concentration of 0.5% zinc by weight of the composition, e.g., after 4 days of agitation.

The present disclosure also provides, in another embodiment, an oral care composition (Composition 2) obtainable by combining a source of zinc ions and a source of citrate ions in a ratio of from 1.7:1 to 2.3:1, e.g., from 1.9:1 to 2.1:1, or in a ratio of about 2:1, during the manufacture of the composition. In further embodiments, the present disclosure provides:

2.1 Composition 2, obtained by combining a source of zinc ions and a source of citrate ions in a ratio of from 1.7:1 to 2.3:1, e.g., from 1.9:1 to 2.1:1, or in a ratio of about 2:1.

2.2 Composition 2 or 2.1, obtainable by adjusting the pH of the composition to from pH 4.6 to 6.2, for example, from pH 5 to 6, or about pH 5.4.

2.3 Composition 2.2, obtained by adjusting the pH of the composition to from pH 4.6 to 6.2, for example, from pH 5 to 6, or about pH 5.4.

2.3 Composition 2 or any of 2.1-2.3, wherein the source of zinc ions is zinc oxide or zinc chloride, and wherein the source of citrate ions is citric acid or sodium citrate.

2.4 Composition 2 or any of compositions 2.1-2.4, wherein the source of zinc ions and the source of citrate ions are combined in a substantially aqueous solution (e.g., from 20% to 100% water by volume) during manufacture of the composition.

The disclosure additionally provides a method of treatment or prophylaxis of a disease or condition of the oral cavity comprising contacting an oral cavity surface of a patient in need thereof with an oral care composition comprising zinc ions and citrate ions in approximately a 2:1 ratio, e.g., with any of Compositions 1, et seq.; for example, wherein the disease or condition of the oral cavity is halitosis or gingivitis.

The disclosure additionally provides the use of zinc and citrate in the manufacture of an oral care composition comprising zinc ions and citrate ions in approximately a 2:1 ratio, e.g., any of Compositions 1, et seq., e.g., for use in a method of treatment or prophylaxis of a disease or condition of the oral cavity, for example, wherein the disease or condition of the oral cavity is halitosis or gingivitis.

The disclosure additionally provides a method of enhancing the bioavailability of zinc in an oral care formulation, comprising providing zinc ions and citrate ions in approximately a 2:1 ratio, e.g., as in any of Compositions 1, et seq.

In certain embodiments, the composition comprises zinc and citrate and further comprises a monodentate anion ligand, wherein the molar ratio of zinc to citrate to anion is about 2:1:1. The anion in a particular embodiment is chloride, which may be provided by any suitable salt, for example, sodium chloride, potassium chloride or zinc chloride, or by a suitable amount of an acid, for example, hydrochloric acid.

The inventors have further discovered that the pH of the composition plays an important role in the formation of preferred complexes and the availability of zinc for uptake. The optimal pH for formation of the zinc-citrate—anion complex is about pH 5.4. Thus, the pH of the compositions is optimally from 4.6 to 8.6, more preferably 4.6 to 6.2, e.g., 5 to 6, for example, about 5.4.

In some embodiments, the source of zinc ions is selected from zinc chloride, zinc citrate, zinc oxide, zinc lactate, zinc nitrate, zinc acetate, zinc gluconate, zinc glycinate, zinc sulfate, zinc oleate, zinc hydroxide, zinc carbonate, or zinc peroxide. Zinc ions are considered to be zinc in solution either in free ion form ($Zn^{++}$), or in soluble complex form, e.g., as in the putative di-zinc/citrate/chloride complex $[Zn_2(citrate)]^+Cl^-$.

Both insoluble and soluble zinc salts may be used, alone or in combination, although the use of soluble zinc salts is preferred (zinc salts with aqueous solubility greater than 0.01 g/L at 20° C.). Where poorly soluble zinc salts are used, greater amounts may be required to provide the desired 2:1 ratio of zinc ions to citrate ions. Preferred zinc salts include zinc chloride, zinc citrate, zinc oxide and zinc nitrate. In some embodiments, the composition comprises two or more different zinc salts. In some embodiments, a mixture of zinc chloride and zinc citrate is used. In other embodiments, a mixture of zinc oxide and zinc citrate is used.

The inventors have found that the use of a 2:1 molar ratio of zinc ions to citrate ions results in an oral care composition with significantly higher bioavailable zinc compared to other zinc-citrate ratios. As a result, in the present disclosure, the concentration of total zinc necessary to achieve an antimicrobial effect is less than in the prior art. The present disclosure provides a composition with a total zinc concentration of 0.01% to 1.0% by weight. In one embodiment, the total zinc content is 0.5% by weight or less. In some embodiments, the total zinc content is about 0.33% by weight, or about 0.25% by weight, or about 0.1% by weight. For a toothpaste composition, a preferred zinc concentration is 0.1% to 0.5% by weight, more preferably about 0.33% by weight. For a mouthwash composition, a preferred zinc concentration is 0.01% to 0.05% by weight, more preferably about 0.03% by weight.

In some embodiments, the citrate source is selected from citric acid, or a mono-, di-, or tri-basic salt of citric acid (e.g., sodium citrate, potassium citrate, magnesium citrate, zinc citrate, calcium citrate). Preferred sources of citrate include citric acid, zinc citrate, sodium citrate and potassium citrate. More preferred are citric acid, zinc citrate and sodium citrate.

In some embodiments, the composition is free of polyphosphates, polyphosphonates, pyrophosphates, and/or phosphates, in their free acid or salt forms.

In some embodiments, the oral care composition of the present disclosure is a toothpaste, or a tooth powder, or a mouthwash. Where the composition is a mouthwash, the total amount of zinc may be relatively lower than in the case of a toothpaste, e.g., 0.1 to 1% by weight in the case of the toothpaste, or 0.01% to 0.1% by weight in the case of a mouthwash.

In some embodiments, the compositions further comprise one or more components selected from a fluoride ion source; a tartar control agent; a buffering agent; an antibacterial agent; an abrasive; and a combination of two or more thereof.

Some embodiments provide compositions wherein at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

Other optional additives may be included. Among such optional additives, included are those provided in order to change appearance or aesthetic appeal, and/or to preserve the final product, and/or for taste/cosmetic appeal and/or as therapeutic and prophylactic ingredients for oral health, prevention or treatment of a condition or disorder of hard or soft tissue of the oral cavity, or the prevention or treatment of a physiological disorder or condition.

Some embodiments provide a composition wherein a preservative is present. In some embodiments, the preservative is selected from parabens, potassium sorbate, benzyl alcohol, phenoxyethanol, polyaminopropyl biguanide, caprylic acid, propylene glycol caprylate, glyceryl caprylate, sodium benzoate and cetylpyridinium chloride. In some embodiments, the preservative is present at a concentration of 0.0001 to 1%, by weight.

Colorants, such as dyes, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cycl-ohexadienimine], FD&C Blue No. 1 (disodium salt of dibenzyldiethyl-di-amino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

Flavoring agents include, but are not limited to, natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavoring agents can be used individually or in admixture. Commonly used flavors include mints such as peppermint, artificial vanilla, cinnamon derivatives, and various fruit flavors, whether employed individually or in admixture. Generally, any flavoring agent or food additive, such as those described in Chemicals Used in Food Processing, publication 1274 by the National Academy of Sciences, pages 63-258, may be used. Typically, flavoring agents, if included, are present at a concentration of from 0.01 to 1%, by weight. In some embodiments, the flavoring agent may be present at a concentration of about 0.2%, by weight.

Sweeteners include both natural and artificial sweeteners. Suitable sweeteners include water soluble sweetening agents such as monosaccharides, disaccharides and polysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, sucralose, cyclamate salts, dipeptide based sweeteners, such as L-aspartic acid derived sweeteners, including L-aspartyl-L-phenylalanine methyl ester (aspartame). In general, the effective amount of sweetener is utilized to provide the level of sweetness desired for a particular composition, which will vary with the sweetener selected. This amount will normally be from 0.001 to 5%, by weight. In some embodiments, the sweetener is sodium saccharin and is present at a concentration of about 0.01%, by weight.

Whitening agents, materials which effect whitening of a tooth surface to which it is applied, may be incorporated into the compositions of the present invention. Such agents include hydrogen peroxide and urea peroxide, high cleaning silica, preservatives, silicones, and chlorophyll compounds. In various embodiments, the compositions of this invention comprise a peroxide whitening agent (e.g., comprising a peroxide compound). A peroxide compound is an oxidizing compound comprising a bivalent oxygen-oxygen group. Peroxide compounds include peroxides and hydroperoxides, such as hydrogen peroxide, alkali and alkaline earth metal peroxides, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more whitening agents are optionally present in a tooth-whitening effective total amount. In some embodiments the whitening agent is separated from the aqueous carrier. In some embodiments the whitening agent is separated from the aqueous carrier by encapsulation of the whitening agent.

Optionally, breath freshening agents may be provided. Any orally acceptable breath freshening agent can be used. One or more breath freshening agents are optionally present in a breath freshening effective total amount.

Other embodiments provide compositions wherein at least one of the one or more components is a tartar control agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. In some embodiments, a phosphate is present at a concentration of from 0.01 to 10%, by weight. In some embodiments, a phosphate is present at a concentration of about 1%, by weight.

Some embodiments provide compositions wherein a buffering agent is present. In some embodiments, sodium phosphate monobasic is present at a concentration of from 0.01 to 5%, by weight. In some embodiments, sodium phosphate monobasic phosphate is present at a concentration of about 1%, by weight. In some embodiments, sodium phosphate dibasic is present at a concentration of from 0.01 to 5%, by weight. In some embodiments, sodium phosphate dibasic phosphate is present at a concentration of about 0.15%, by weight. In some embodiments, either an inorganic acid (e.g., hydrochloric acid), an inorganic base (e.g., sodium hydroxide), or a combination thereof, is added to achieve a desired pH for the composition.

Other optional additives include antimicrobial (e.g., antibacterial) agents. Any orally acceptable antimicrobial agent can be used, including Triclosan (5-chloro-2-(2,4-dichlorophenoxy)phenol); 8-hydroxyquinoline and salts thereof, stannous ion sources such as stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride,); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; biguanides; phenolics; piperidino derivatives such as delmopinol and octapinol; magnolia extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is provided in U.S. Pat. No. 5,776,435, Gaffar, et al., issued Jul. 7, 1998. In some embodiments, the antimicrobial agent is present at a concentration of from about 0.001 to about 1%, by weight. In some embodiments, the antimicrobial agent is cetylpyridinium chloride. In some embodiments, cetylpyridinium chloride is present at a concentration of from 0.001 to 1%, by weight. In other embodiments, cetylpyridinium chloride is present at a concentration of about 0.05%, by weight.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, a saliva stimulating agent, useful, for example, in amelioration of dry mouth, may be included. Any orally acceptable saliva stimulating agent can be used, including, without limitation, food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including, without limitation, stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium salts, such as potassium citrate, potassium chloride, potassium tartrate, potassium bicarbonate, potassium oxalate, potassium nitrate, and strontium salts, and mixtures thereof.

Optional additives also include vitamins, herbs and proteins. Vitamins include Vitamins C and D, thiamine, riboflavin, calcium pantothenate, niacin, folic acid, nicotinamide, pyridoxine, cyanocobalamin, para-aminobenzoic acid, bioflavonoids, pantheon, retinyl palmitate, tocopherol acetate, and mixtures thereof. Herbs such as *Chamomilla recutita, Mentha piperita, Salvia officinalis*, and *Commiphora myrrha* may optionally be included. Suitable proteins include milk proteins and enzymes such as peroxide-producing enzymes, amylase, plaque-disrupting agents such as papain, glucoamylase, and glucose oxidase.

Some embodiments provide a method of treating or preventing a disease or condition of the oral cavity comprising contacting an oral cavity surface of a patient in need thereof with any one of the compositions described herein. In other embodiments, the disease or condition of the oral cavity is halitosis or gingivitis. In some embodiments, the present invention provides a method of reducing volatile sulfur compounds in the oral cavity of a subject in need thereof. In further embodiments, the present invention provides a method for increasing the delivery of a metal ion to an oral cavity surface.

In certain embodiments, the compositions described herein can be used, for example, for cavity prevention, whitening, plaque prevention or reduction, gingivitis prevention or reduction, tartar control, breath malodor prevention or reduction, and stain prevention.

In some embodiments, the composition further comprises a carrier. The specific composition of the carrier preferably depends on the intended use of the composition. In various embodiments, the carrier is aqueous, comprising from 5% to 95%, by weight, water or from 10% to 70%, by weight, water. In other embodiments, the carrier is substantially non-aqueous. In a dentifrice carrier, water content can be from 5% to 70%, from 10% to 50%, or from 20% to 40%, by weight.

The carrier may comprise any of a variety of materials, including emulsifiers, thickeners, fillers, and preservatives. In some embodiments, the carrier may include a functional or active material, such as those described above.

In some embodiments, the carrier comprises a humectant, such as glycerin, sorbitol or an alkylene glycol such as polyethylene glycol or propylene glycol. In some embodiments, the carrier comprises a humectant at a level of from about 10 to about 80% by weight, or about 20 to about 60% by weight of the composition. Carrier compositions among those useful herein are disclosed in U.S. Pat. No. 5,695,746 to Garlick, Jr., et al. and U.S. Pat. No. 4,839,157 to Mei-King Ng et al.

Thickeners or gelling agents useful herein include inorganic, natural or synthetic thickeners or gelling agents. In some configurations, the carrier comprises the thickener and gelling agent at total levels of from 0.1 to 15% by weight, or from 0.4 to 10% by weight of the composition. Examples of thickeners and gelling agents useful herein include inorganic thickening silicas such as: an amorphous silica, for example Zeodent® 165 (Huber Corporation); Irish moss; iota-carrageenan; gum tragacanth; or polyvinylpyrrolidone.

In certain embodiments, the carrier comprises an abrasive or polishing agent, such as a silica, a calcined alumina, sodium bicarbonate, calcium carbonate, dicalcium phosphate or calcium pyrophosphate. In various embodiments, the carrier is clear. In various embodiments, the carrier comprises an abrasive at a level of from 5 to 70% by weight of the composition.

In some embodiments, the compositions comprise a surfactant or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate; and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments, the surfactant is present at a concentration of from 0.3 to 5% by weight of composition, or 0.5 to 3% by weight of composition.

Compositions as described herein can be prepared according to methods readily known to those skilled in the art.

Embodiments of the present invention are further described in the following examples. The examples are merely illustrative and do not in any way limit the scope of the invention as described and claimed.

EXAMPLES

Example 1

Table 1 provides a comparison of two exemplary formulations of the present invention. Soluble zinc analysis was performed as described herein below, and the results show that Formulation A (pH 5.9) has significantly higher soluble zinc content than Formulation B (pH 6.7).

TABLE 1

| Description | Formulation A | Formulation B |
|---|---|---|
| DEMINERALIZED WATER | 13 | 13 |
| SORBITOL - 70% SOLN | 26 | 26 |
| GLYCERIN | 30.464 | 30.464 |
| ZINC OXIDE | 0.31 | 0.31 |
| Citric acid anhydrous | 0.366 | 0.366 |
| 35% Hydrochloric Acid | 0.3 | 0.3 |
| SODIUM FLUORIDE | 0.32 | 0.32 |
| Non-ionic Surfactant | 1.6 | 1.6 |
| Zwitterionic Surfactant | 3.34 | 3.34 |
| XANTHAN GUM | 0.5 | 0.5 |
| SODIUM CMC | 0.8 | 0.8 |
| SILICA-ABRASIVE | 6 | 6 |
| HIGH CLEANING SILICA | 10 | 10 |
| SILICA-THICKENER | 5 | 5 |
| sweetener | 0.3 | 0.3 |
| Flavor | 1.2 | 1.2 |
| TITANIUM DIOXIDE | 0.5 | 0.5 |
| 50% Sodium hydroxide | 0 | q.c. to pH 6.7 |
| Total Components | 100 | 100 |
| Water | 21.0 | 21.0 |
| pH | 5.9 | 6.7 |

TABLE 1-continued

| Description | Formulation A | Formulation B |
|---|---|---|
| Soluble Zinc analysis (% of total zinc level): | 98% | 70% |

Example 2

The soluble zinc concentration of various zinc-citrate formulations is evaluated as follows. A 0.906% w/v sodium chloride solution in distilled water is prepared. Eleven test samples are prepared by combining in the sodium chloride solution zinc oxide and zinc citrate trihydrate in specific ratios to achieve molar ratios of zinc to citrate of 10:1 to 1.5:1. All samples are adjusted to have a net zinc concentration of 0.5% w/w. The samples are agitated for 2-5 days. After centrifuging, the supernatant is analyzed for soluble zinc.

The results are shown in the following table. The 2:1 ratio of zinc to citrate is shown to result in the highest concentration of soluble zinc.

TABLE 2

| Run | Zn:Citrate | Days | Soluble Zn (ppm) |
|---|---|---|---|
| 1 | 10.0:1 | 5 | 990 |
| 2 | 9.0:1 | 5 | 1050 |
| 3 | 8.0:1 | 5 | 1300 |
| 4 | 7.0:1 | 5 | 1400 |
| 5 | 4.0:1 | 4 | 2250 |
| 6 | 3.0:1 | 4 | 2900 |
| 7 | 2.5:1 | 4 | 3500 |
| 8 | 2.25:1 | 4 | 3450 |
| 9 | 2.0:1 | 4 | 3700 |
| 10 | 1.75:1 | 4 | 3400 |
| 11 | 1.50:1 | 4 | 1400 |

Example 3

The uptake of zinc in Vitro skin was evaluated using the following test procedures. Vitro-skin (IMS Inc., Portland, Me.) is cut into uniform circles of diameter between 10 to 14 mm, such as by using a cork borer. The Vitro-skin circles are rinsed (in bulk) 3 times with hexanes for 5 minutes. Air dry to evaporate hexanes. The Vitro-skin is soaked in sterilized and cleared saliva overnight in a disposable polystyrene Falcon tube (mfc. code 352057). 1 mL of saliva per tissue is used, and this is performed in triplicate. The saliva is aspirated, and 1 mL of 1:2 paste slurry is added and incubated for 2 minutes in a 37° C. water bath. The slurry is aspirated and rinsed 3 times with 5 mL of deionized water for 10 seconds each time, using a vortexer for mixing. The tissue is transferred into a new polystyrene Falcon tube (mfc. code 352095). 1 mL of concentrated nitric acid is added to the tissue and it is incubated overnight. The tissue should dissolve completely. Enough deionized water is added to fill the tube to the 10 mL line. The tube is shaken well, and is then submitted for AA zinc analysis. The obtained level of zinc (typically in ppm) must be multiplied by the total volume (10× in this case) to get a figure in μg of zinc per tissue ($U_T$). Table 3 (below) describes the data generated in the Vitro-skin experiments described above using zinc ion solutions. Zinc chloride solution is prepared by adding the appropriate amount of the salt to deionized water and stirring for 30 minutes. Zinc citrate (commercial) solution is prepared by adding the appropriate amount of the salt to deionized water and stirring for 30 minutes (the zinc citrate does not completely dissolve). Zinc citrate (prepared) is generated in situ by combining zinc oxide and citric acid at a 3:2 ratio in deionized water and stirring for 30 minutes (fully soluble). Solutions at a 2:1 zinc to citrate molar ratio are prepared by combining, zinc oxide and trisodium citrate dihydrate in deionized water at a 2:1 molar ratio, adjusting the pH using hydrochloric acid and stirring for 30 minutes (fully soluble). All four test solutions have a net concentration of 0.39% by weight of zinc.

To calculate uptake of zinc per square centimeter, the following formula can be used: $U_R = 2*U_T/(\pi*d^2)$ [μg/cm²]
wherein: $U_R$=(relative) zinc uptake per square centimeter of Vitro-skin (both sides)
$U_T$=zinc uptake per tissue
d=diameter of the tissue in centimeters

TABLE 3

| Formula (all concentrations 0.39% w/w Zn) | Zn uptake to Vitro-skin (μg/cm²) | Standard Deviation |
|---|---|---|
| Zinc Chloride | 41.9 | 3.7 |
| 2:1 Zinc:Citrate (pH 5.5) | 53.9 | 2.3 |
| 2:1 Zinc:Citrate (pH 8.5) | 12.5 | 2.2 |
| Zinc Citrate (commercial) | 38.1 | 2.0 |
| Zinc Citrate (prepared) | 49.6 | 3.0 |

$ZnCl_2 + Zn_3Cit_2 = 2(Zn_2CitCl)$, so $Zn_2CitCl$ can be viewed as an equimolar mixture of zinc chloride and zinc citrate. One therefore would expect the uptake for the $Zn_2CitCl$ to be somewhere between the uptake for zinc chloride and zinc citrate, but in fact, it is significantly higher than either.

The uptake for the 2:1 zinc-citrate ratio is the same whether the zinc and citrate are provided by zinc oxide and sodium citrate or from other sources, such as zinc oxide and citric acid, or zinc chloride and citric acid, provided that the pH is in a range to permit formation of the desired $Zn_2CitCl$ complex.

Example 4

The antibacterial activity of the $Zn_2CitCl$ (dizinc citrate chloride) complex was compared against zinc citrate (ZnCit) using the resazurin bacterial inhibition assay. In order to test this hypothesis, we used an assay we have developed based on the metabolic indicator dye resazurin. Previous work has demonstrated that this assay is a useful tool for understanding the relative bioavailablity and bioactivity of simple solutions of zinc compounds. A five species, planktonic mix of representative oral species is used in this assay (*Actinomyces viscosus, Lactobacillus casei, Streptococcus oralis, Fusobacterium nucleatum,* and *Veillonella parvula*). Bacteria are incubated with the test solution for 1 h prior to staining with 50 μg/ml of resazurin solution. When viable, metabolically active bacteria are incubated with resazurin, the blue, non-fluorescent dye is reduced by the bacteria to the pink fluorescent dye resrufin. Fluorescence of test samples are read at 560 nm excitation/590 nm emission and compared to the fluorescence of standard mixes of live and dead bacteria to determine the percentage of the initial population that remained viable following treatment. Samples were tested at a final concentration of 1% elemental Zn for each compound indicated.

| Compound | Zn:Cit | % viability |
|---|---|---|
| sodium zinc citrate | 1:1 | 5.9 |
| sodium dizinc citrate chloride | 2:1 | 2.0 |
| basic sodium zinc citrate | 1:1 | 7.0 |
| basic sodium dizinc citrate chloride | 2:1 | 3.3 |

As can be seen from the data, the dizinc citrate chlorides of the invention provided greater antibacterial activity than zinc citrate.

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising: a source of zinc ions and a source of citrate ions, wherein the ratio of zinc ions to citrate ions is from 1.7:1 to 2.5:1 on a molar basis; wherein the composition comprises $[Zn_2(citrate)]^+Cl^-$.

2. An oral care composition according to claim 1, wherein the ratio of zinc ions to citrate ions is from 1.9:1 to 2.1:1, on a molar basis.

3. An oral care composition according to claim 1, further comprising a monodentate anion, wherein the ratio of zinc ions to citrate ions to anion is about 2:1:1 on a molar basis.

4. An oral care composition according to claim 1, wherein the pH of the composition is from 4.6 to 8.6.

5. An oral care composition according to claim 1, wherein the zinc source is selected from zinc chloride, zinc citrate, zinc oxide, zinc lactate, zinc nitrate, zinc acetate, zinc gluconate, zinc glycinate, zinc sulfate, zinc oleate, zinc hydroxide, zinc carbonate, zinc peroxide, or a combination of two or more thereof.

6. An oral care composition according to claim 1, wherein the zinc source is selected from zinc chloride, zinc citrate or zinc oxide.

7. An oral care composition according to claim 1, comprising zinc chloride and zinc citrate.

8. An oral care composition according to claim 1, comprising zinc oxide and zinc citrate.

9. An oral care composition according to claim 1, wherein the citrate source is selected from citric acid or a mono-, di- or tri-basic citrate salt.

10. An oral care composition according to claim 1, wherein the citrate source is citric acid or sodium citrate.

11. An oral care composition according to claim 1, comprising zinc oxide and citric acid.

12. An oral care composition according to claim 1, comprising zinc chloride and sodium citrate.

13. An oral care composition according to claim 1, wherein the total zinc concentration is from 0.01% to 1.0% by weight of the composition.

14. An oral care composition according to claim 1, wherein the composition is free of polyphosphates, polyphosphonates, pyrophosphates and/or phosphates.

15. An oral care composition according to claim 1, further comprising one or more components selected from a fluoride ion source; a tartar control agent; a buffering agent; an antibacterial agent; an abrasive; and a combination of two or more thereof.

16. The composition of claim 15, wherein at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

17. An oral care composition according to claim 1, wherein the composition is a toothpaste, tooth powder, or mouthwash.

18. A method of treating a disease or condition of the oral cavity comprising contacting an oral cavity surface of a patient in need thereof with the composition of claim 1.

19. The method of claim 18, wherein the disease or condition of the oral cavity is halitosis or gingivitis.

20. The composition of claim 3, wherein the monodentate anion is chloride anion.

* * * * *